United States Patent
Ishikawa et al.

(10) Patent No.: US 10,160,722 B2
(45) Date of Patent: Dec. 25, 2018

(54) METHOD FOR PRODUCING PERFLUOROALKANESULFONYL PHENOL COMPOUNDS

(71) Applicant: SUMITOMO CHEMICAL COMPANY, LIMITED, Tokyo (JP)

(72) Inventors: Junichi Ishikawa, Takarazuka (JP); Koji Hagiya, Osaka (JP); Mitsunobu Kawamura, Osaka (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 15/575,693

(22) PCT Filed: Jun. 1, 2016

(86) PCT No.: PCT/JP2016/066128
§ 371 (c)(1),
(2) Date: Nov. 20, 2017

(87) PCT Pub. No.: WO2016/194929
PCT Pub. Date: Dec. 8, 2016

(65) Prior Publication Data
US 2018/0290970 A1 Oct. 11, 2018

(30) Foreign Application Priority Data

Jun. 4, 2015 (JP) ................................. 2015-113690

(51) Int. Cl.
| C07C 315/00 | (2006.01) |
| C07C 315/04 | (2006.01) |
| C07C 315/02 | (2006.01) |
| C07C 317/36 | (2006.01) |

(52) U.S. Cl.
CPC .................. *C07C 315/00* (2013.01)

(58) Field of Classification Search
CPC ... C07C 315/00; C07C 315/04; C07C 315/02; C07C 317/36
See application file for complete search history.

(56) References Cited

U.S. PATENT DOCUMENTS

| 3,876,707 A | 4/1975 | Menet |
| 5,565,689 A | 10/1996 | Clavel et al. |
| 2015/0313234 A1 | 11/2015 | Takahashi et al. |
| 2017/0137377 A1 | 5/2017 | Ueki et al. |

FOREIGN PATENT DOCUMENTS

| JP | 49-7223 A | 1/1974 |
| JP | 1-149762 A | 6/1989 |
| JP | 4-41474 A | 2/1992 |
| WO | WO 2014/104407 A1 | 7/2014 |
| WO | WO 2015/198850 A1 | 12/2015 |

OTHER PUBLICATIONS

Andreades, et al., "Aryl Fluoroalkyl Sulfides. II. Preparation by Condensation of Trifluoromethanesulfenyl Chloride with Aromatic Systems", The Journal of Organic Chemistry, 1964, vol. 29, No. 4, pp. 898-900.
Avdeenko et al., "Reactions of N-Aryl(methyl, trifluoromethy)sulfonyl-1,4-benzoquinone Monoimines with Sodium Sulfinates", Russian Journal of Organic Chemistry, 2012, vol. 48, No. 2, pp. 221-233.
Bailey et al., "Enzymic Oxidation of o-Aminophenols", Chemical Communications, 1967, pp. 408-409.
International Search Report for PCT/JP2016/066128 (PCT/ISA/210) dated Sep. 6, 2016.
International Preliminary Report on Patentability and English translation of the Written Opinion of the International Searching Authority (Forms PCT/IB/373 and PCT/ISA/237), for International Application No. PCT/JP2016/066128, dated Dec. 5, 2017.

*Primary Examiner* — Jafar F Parsa
(74) *Attorney, Agent, or Firm* — Birch, Stewart, Kolasch & Birch, LLP

(57) ABSTRACT

A compound represented by formula (3):

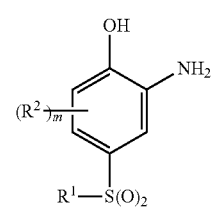

(3)

(wherein $R^1$ represents a C1-C6 perfluoroalkyl group, $R^2$ represents a C1-C6 alkyl group, and m represents an integer of 0 to 3)
or a salt thereof, which is useful as a production intermediate of pharmaceuticals and agrochemicals, can be produced by reacting an alkali metal salt or zinc salt of a C1-C6 perfluoroalkanesulfinic acid with 2-aminophenol optionally substituted by 1 to 3 C1-C6 alkyl groups or a salt thereof in the presence of an oxidizing agent.

8 Claims, No Drawings

METHOD FOR PRODUCING PERFLUOROALKANESULFONYL PHENOL COMPOUNDS

TECHNICAL FIELD

The present invention relates to a method for producing a perfluoroalkanesulfonylphenol compound useful as a production intermediate of pharmaceuticals and agrochemicals.

BACKGROUND ART

Perfluoroalkanesulfonylphenol compounds are useful as production intermediates of pharmaceuticals and agrochemicals (see WO2014/104407).

For the production thereof, a method of producing a perfluoroalkanesulfanylphenol compound from a phenol compound and then oxidizing the perfluoroalkanesulfanylphenol compound is commonly used (see WO2014/104407 and Journal of Organic Chemistry, 1964, vol. 29, p. 898 to 900).

SUMMARY OF THE INVENTION

The present invention provides a novel method for producing a perfluoroalkanesulfonylphenol compound.

According to the present invention, an alkali metal salt or zinc salt of a C1-C6 perfluoroalkanesulfinic acid and 2-aminophenol optionally substituted by 1 to 3 C1-C6 alkyl groups or a salt thereof are reacted in the presence of an oxidizing agent, whereby a compound represented by formula (3):

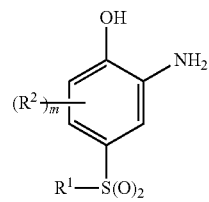

(3)

(wherein $R^1$ represents a C1-C6 perfluoroalkyl group, $R^2$ represents a C1-C6 alkyl group, and m represents an integer of 0 to 3)
(hereinafter referred to as Compound (3)) or a salt thereof can be produced.

MODE FOR CARRYING OUT THE INVENTION

The alkali metal salt of a C1-C6 perfluoroalkanesulfinic acid used in the present invention is a sulfinate represented by formula (1a):

(1a)

(wherein $R^1$ represents a C1-C6 perfluoroalkyl group, and M represents an alkali metal)
and a zinc salt of a C1-C6 perfluoroalkanesulfinic acid is a sulfinate represented by formula (1b):

(1b)

(wherein $R^1$ has the same meaning as described above).

Examples of the C1-C6 perfluoroalkyl group include a trifluoromethyl group, a pentafluoroethyl group, a heptafluoropropyl group, a nonafluorobutyl group, a perfluoropentyl group and a perfluorohexyl group, among which C1-C3 perfluoroalkyl group is preferred.

The alkali metals are lithium, sodium, potassium, rubidium, and cesium.

Examples of the alkali metal salt of a C1-C6 perfluoroalkanesulfinic acid include sodium trifluoromethanesulfinate, potassium trifluoromethanesulfinate, sodium pentafluoroethanesulfinate, potassium pentafluoroethanesulfinate, sodium heptafluoropropanesulfinate, potassium heptafluoropropanesulfinate, sodium nonafluorobutanesulfinate, and sodium tridecafluorohexanesulfinate. The sulfinate can be obtained by purchase of a commercially available product, synthesis according to the method described in WO 2011/108622, and the like.

Examples of the zinc salt of a C1-C6 perfluoroalkanesulfinic acid include zinc bis(trifluoromethanesulfinate), zinc bis(pentafluoroethanesulfinate), and zinc bis(tridecafluorohexanesulfinate). The sulfinate can be obtained by purchase of a commercial product, synthesis according to the method described in Nature (London, United Kingdom) (2012), 492 (7427), 95-99), and the like.

2-Aminophenol optionally substituted by 1 to 3 C1-C6 alkyl groups is a compound represented by formula (2):

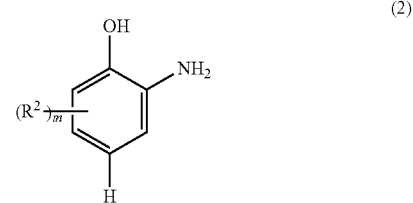

(2)

(wherein $R^2$ represents a C1-C6 alkyl group, and m represents an integer of 0 to 3)
(hereinafter referred to as Compound (2)), the C1-C6 alkyl group may be linear or branched, and examples thereof include a methyl group, an ethyl group, a propyl group, an isopropyl group, a butyl group, a sec-butyl group, a tert-butyl group, a pentyl group, a 2-pentyl group, a neopentyl group, a 4-methyl-2-pentyl group, a hexyl group, and a 3-methylpentyl group.

Examples of Compound (2) include 2-aminophenol, 2-amino-3-methylphenol, 2-amino-5-methylphenol, 2-amino-6-methylphenol, 2-amino-3-ethylphenol, 2-amino-5-ethylphenol, and 2-amino-6-ethylphenol.

The salt of 2-aminophenol optionally substituted by a C1-C6 alkyl group means an acid addition salt of Compound (2), and specific examples thereof include addition salts of inorganic acids such as hydrochloric acid and sulfuric acid, and addition salts of organic acids such as organic sulfonic acids such as methanesulfonic acid and p-toluenesulfonic acid and organic carboxylic acids such as acetic acid and trifluoroacetic acid.

The addition salt of an inorganic acid is obtained by adding 1 to 10 mol of an inorganic acid such as hydrochloric acid or sulfuric acid to 1 mol of Compound (2) in an organic solvent (for example, an alcohol such as ethanol), and also can be generated in the reaction system.

The addition salt of an organic acid is obtained by adding 1 to 10 mol of an organic acid such as an organic sulfonic acid such as methanesulfonic acid or p-toluenesulfonic acid or an organic carboxylic acid such as acetic acid or trifluoroacetic acid to 1 mol of Compound (2) in an organic solvent (for example, an alcohol such as ethanol), and also can also be generated in the reaction system.

The acid addition salt of Compound (2) can be led to Compound (2) by neutralization with a base such as an aqueous sodium hydroxide solution.

In the present invention, examples of the oxidizing agent include oxygen; persulfates such as potassium persulfate and ammonium persulfate; peroxides such as hydrogen peroxide and tert-butyl hydroperoxide; transition metal compounds such as trivalent iron compounds, divalent copper compounds and manganese compounds; hypervalent iodine compounds such as sodium periodate; quinone compounds such as benzoquinone, naphthoquinone, anthraquinone and chloranil; and salts of halogen oxoacids such as sodium hypochlorite and sodium chlorite. Further, these may be used in combination of two or more.

Examples of the trivalent iron compounds include iron (III) chloride, potassium hexacyanoferrate(III), and iron(III) oxide; and examples of the divalent copper compounds include copper(II) sulfate, and copper(II) chloride. Examples of the manganese compound include manganese dioxide.

Among the above oxidizing agents, oxidizing agents selected from the group consisting of potassium persulfate, ammonium persulfate, tert-butyl hydroperoxide, iron(III) chloride, iron(III) oxide, manganese dioxide and copper(II) sulfate are preferable, and iron(III) oxide (α-crystal, β-crystal, γ-crystal, ϵ-crystal) is more preferable.

When oxygen is used as the oxidizing agent, the reaction may be carried out in the air, and other oxidizing agents may be used in combination.

The reaction for producing Compound (3) or a salt thereof by reacting the alkali metal salt or zinc salt of a C1-C6 perfluoroalkanesulfinic acid with Compound (2) or a salt thereof in the presence of an oxidizing agent is usually carried out in a solvent. Examples of the solvent include aromatic hydrocarbons such as toluene, xylene, cumene, monochlorobenzene and tetralin; aliphatic hydrocarbons such as hexane, heptane, octane, nonane and cyclohexane; sulfur-containing compounds such as dimethyl sulfoxide and sulfolane; ethers such as tetrahydrofuran, 2-methyltetrahydrofuran, cyclopentyl methyl ether, tert-butyl methyl ether, monoglyme and diglyme; organic carboxylic acids such as acetic acid, propionic acid, butyric acid and ethylhexanoic acid; amides such as N,N-dimethylacetamide, N,N-dimethylformamide and N-methylpyrrolidone; nitriles such as acetonitrile and propylnitrile; esters such as methyl acetate and ethyl acetate; ketones such as acetone and methyl isobutyl ketone; alcohols such as methanol, ethanol and propanol, and mixtures thereof. Among them, organic carboxylic acid and nitrile are preferred.

The amount of the solvent is usually from 1 to 100 times by weight and preferably from 1 to 30 times by weight, of Compound (2).

The sulfinate is usually used in a proportion of 1 mol to 5 mol, to 1 mol of Compound (2).

The oxidizing agent is usually used in a proportion of 1 mol to 5 mol, to 1 mol of Compound (2).

The reaction temperature is usually in the range of −20° C. to 200° C., and the reaction time is usually in the range of 1 minute to 24 hours.

It is preferable to carry out the reaction by adding a strong acid. Examples of the strong acid include sulfuric acid, methanesulfonic acid and hydrochloric acid, and the strong acid is usually used in a proportion of 1 mol to 10 mol, to 1 mol of Compound (2).

After completion of the reaction, Compound (3) can be isolated by subjecting the reaction mixture to crystallization or the like. The obtained Compound (3) can be further purified by distillation, recrystallization, extraction, chromatography and the like.

In addition, when a trivalent iron compound (e.g., iron (III) chloride, iron(III) oxide) is used as the oxidizing agent, a reducing agent such as a metal hydride is added to the reaction system after completion of the reaction, iron in the system resulting from the trivalent iron compound can be removed by filtration.

Examples of the metal hydride include lithium aluminum hydride, lithium borohydride, sodium borohydride, lithium hydride, potassium hydride and calcium hydride, and lithium aluminum hydride, lithium borohydride and sodium borohydride are preferred.

The metal hydride is preferably added in a proportion of 0.1 mol to 5 mol, to 1 mol of the trivalent iron compound to be added.

Compound (3) can also be isolated in the form of an acid addition salt. Specific examples of the acid addition salt include addition salts of inorganic acids such as hydrochloric acid and sulfuric acid, and addition salts of organic acids such as organic sulfonic acids such as methanesulfonic acid and p-toluenesulfonic acid, and organic carboxylic acids such as acetic acid and trifluoroacetic acid. In order to isolate these acid addition salts, waste derived from the oxidizing agent used is removed from the reaction mixture after completion of the reaction, and then an acid is added to crystallize the acid addition salt.

Examples of Compound (3) to be obtained include 2-amino-4-trifluoromethanesulfonyl) phenol, 2-amino-3-methyl-4-trifluoromethanesulfonylphenol, 2-amino-5-methyl-4-trifluoromethanesulfonylphenol, 2-amino-6-methyl-4-trifluoromethanesulfonylphenol, 2-amino-3-ethyl-4-trifluoromethanesulfonylphenol, 2-amino-5-ethyl-4-trifluoromethanesulfonylphenol, 2-amino-6-ethyl-4-trifluoromethanesulfonylphenol, and 2-amino-4-pentafluoroethanesulfonylphenol.

Examples of embodiments of the present invention include the following embodiments.

In the present invention, a method in which the oxidizing agent is one or more oxidizing agents selected from the group consisting of persulfates, peroxides, trivalent iron compounds, divalent copper compounds and manganese compounds.

In the present invention, a method in which the oxidizing agent is one or more oxidizing agents selected from the group consisting of persulfates, peroxides, trivalent iron compounds, divalent copper compounds and manganese compounds, and a strong acid is added.

In the present invention, a method in which the oxidizing agent is one or more oxidizing agents selected from the group consisting of persulfates, peroxides, trivalent iron compounds, divalent copper compounds and manganese compounds, and one or more strong acids selected from the group consisting of sulfuric acid, methanesulfonic acid and hydrochloric acid are added.

In the present invention, a method in which the oxidizing agent is one or more oxidizing agents selected from the group consisting of potassium persulfate, ammonium persulfate, tert-butyl hydroperoxide, iron(III) chloride, iron(III) oxide, manganese dioxide and copper (II) sulfate.

In the present invention, a method in which the oxidizing agent is one or more oxidizing agents selected from the group consisting of potassium persulfate, ammonium persulfate, tert-butyl hydroperoxide, iron(III) chloride, iron(III) oxide, manganese dioxide and copper (II) sulfate, and a strong acid is added.

In the present invention, a method in which the oxidizing agent is one or more oxidizing agents selected from the group consisting of potassium persulfate, ammonium persulfate, tert-butyl hydroperoxide, iron(III) chloride, iron(III) oxide, manganese dioxide and copper (II) sulfate, and one or more strong acids selected from the group consisting of sulfuric acid, methanesulfonic acid and hydrochloric acid are added.

In the present invention, a method in which the oxidizing agent is iron(III) oxide.

In the present invention, a method in which the oxidizing agent is iron(III) oxide, and a strong acid is added.

In the present invention, a method in which the oxidizing agent is iron(III) oxide, and sulfuric acid is added.

In the present invention, a method in which the oxidizing agent is iron(III) oxide, and methanesulfonic acid is added.

In the present invention, a method in which the oxidizing agent is iron(III) oxide and is carried out in acetonitrile.

In the present invention, a method in which the oxidizing agent is iron(III) oxide, and sulfuric acid is added in acetonitrile.

In the present invention, a method in which the oxidizing agent is iron (III) oxide, and methanesulfonic acid is added in acetonitrile.

In the present invention, a method in which the oxidizing agent is manganese dioxide.

In the present invention, a method in which the oxidizing agent is manganese dioxide, and a strong acid is added.

In the present invention, a method in which the oxidizing agent is manganese dioxide, and methanesulfonic acid is added in acetonitrile.

In the present invention, a method in which the oxidizing agent is iron(III) chloride.

In the present invention, a method in which the oxidizing agent is iron(III) chloride, and a strong acid is added.

In the present invention, a method in which the oxidizing agent is iron(III) chloride, and methanesulfonic acid is added.

In the present invention, a method in which the oxidizing agent is oxygen.

In the present invention, a method in which the oxidizing agent is oxygen and iron(III) chloride.

EXAMPLES

Hereinafter, the present invention will be described by way of examples and the like, but the present invention is not limited only to these examples.

The analysis conditions by the internal standard method using high performance liquid chromatography in the examples are as follows.

Analytical instrument: CBM-20A manufactured by Shimadzu Corporation
Mobile phase (A/B): 0.1% Aqueous phosphoric acid/acetonitrile
Column: SUMIPAX ODS Z-CLUE φ 4.6 mm×100 mm (3 μm) manufactured by Sumika Chemical Analysis Service, Ltd.
Column temperature: 40° C.
Flow rate: 1.0 mL/min
UV wavelength: 250 nm
Injection amount: 10 μl
The internal standard substance: Acetanilide
Time program

| Time (min) | Concentration (%) |
|---|---|
| 0 | 10 |
| 40 | 90 |
| 50 | 90 |
| 50.1 | 10 |
| 60 | 10 |

Example 1-1

Under a nitrogen atmosphere, 0.14 mol (15.00 g) of 2-aminophenol, 0.21 mol (32.17 g) of sodium trifluoromethanesulfinate, 60 g of acetonitrile and 0.41 mol (40.41 g) of sulfuric acid were stirred at room temperature for 15 minutes. To the resulting mixture were added 0.27 mol (43.73 g) of iron oxide ($Fe_2O_3$) and 90 g of acetonitrile, followed by stirring at 70° C. for 7 hours. After cooling the reaction mixture to room temperature, 0.08 mol (3.12 g) of sodium borohydride was added thereto, and the mixture was stirred for 30 minutes. Thereafter, 50 g of water was added thereto, the mixture was filtered through Celite (registered trademark), and the filtrate was washed with acetonitrile. The yield was calculated by analyzing a part of the combined solution of the filtrate and the washing liquid by the internal standard method using high performance liquid chromatography. The yield of 2-amino-5-trifluoromethanesulfonylphenol was 54%.

Example 1-2

Under a nitrogen atmosphere, 0.09 mol (10.00 g) of 2-aminophenol, 0.08 mol (12.9 g) of sodium trifluoromethanesulfinate, 100 g of acetonitrile and 0.33 mol (32.33 g) of sulfuric acid were stirred at room temperature for 15 minutes. To the resulting mixture were added 0.18 mol (29.16 g) of iron oxide ($Fe_2O_3$) and 50 g of acetonitrile, followed by stirring at 73° C. for 2 hours. After cooling the reaction mixture to room temperature, 0.05 mol (2.08 g) of sodium borohydride was added thereto, and the mixture was stirred for 30 minutes. Thereafter, 10 g of water was added thereto, the mixture was filtered through Celite (registered trademark), and the filtrate was washed with acetonitrile. The yield was calculated by analyzing a part of the combined solution of the filtrate and the washing liquid by the internal standard method using high performance liquid chromatography. The yield of 2-amino-5-trifluoromethanesulfonylphenol was 78%.

The filtrate and the washing liquid were combined and concentrated, and 75 g of 1 N hydrochloric acid and 100 g of methyl t-butyl ether were added to the resulting oily substance, then the mixture was separated into an organic layer and an aqueous layer. The aqueous layer was extracted with 100 g of methyl t-butyl ether, the resulting organic layers were combined, and 7 g of activated carbon was added. The mixture was stirred for 30 minutes and then filtered, and the filtrate was concentrated. To the resulting oily substance added 10 g of methanol, and the mixture was added to a solution of 35 g of sodium sulfate in 200 g of water while stirring at room temperature, thereby precipitating crystals. The crystals obtained by filtration were dried to obtain 18.1 g of 2-amino-5-trifluoromethanesulfonylphenol having a purity of 73%.

Extraction yield 60%.

The crude crystals (18 g) were stirred with 160 g of 50% aqueous methanol and 5 g of activated carbon at 60° C. for 30 minutes, then the mixture was filtered at 60° C., and methanol was distilled off from the filtrate to obtain precipitated crystals. The crystals were cooled to room temperature and filtered and dried to obtain 12 g of 2-amino-5-trifluoromethanesulfonylphenol having a purity of 90.7%. Isolated yield 50%.

Example 1-3

Iron oxide ($Fe_3O_4$) was heated in the air at 250° C. for 2 hours to obtain iron oxide ($Fe_2O_3$) to be used below.

Under a nitrogen atmosphere, 0.09 mol (10.00 g) of 2-aminophenol, 0.08 mol (12.9 g) of sodium trifluoromethanesulfinate, 100 g of acetonitrile and 0.33 mol (32.33 g) of sulfuric acid were stirred at room temperature for 15 minutes. To the resulting mixture were added 0.18 mol (29.16 g) of the iron oxide ($Fe_2O_3$) prepared above and 50 g of acetonitrile, and the mixture was stirred at 73° C. for 5 hours. After cooling the reaction mixture to room temperature, 0.05 mol (2.08 g) of sodium borohydride was added thereto, and the mixture was stirred for 30 minutes. Thereafter, 50 g of water was added thereto, the mixture was filtered through Celite (registered trademark), and the filtrate was washed with acetonitrile. The yield was calculated by analyzing a part of the combined solution of the filtrate and the washing liquid by the internal standard method using high performance liquid chromatography. The yield of 2-amino-5-trifluoromethanesulfonylphenol was 69%.

Example 2

Under a nitrogen atmosphere, 30.2 mmol (4.72 g) of sodium trifluoromethanesulfinate, 27.5 mmol (3.0 g) of 2-aminophenol and 60 g of acetonitrile were mixed, and 13.27 g of methanesulfonic acid was added dropwise thereto at 5° C. To the resulting mixture was added 55.3 mmol (4.81 g) of manganese dioxide at 5° C. over 8 hours, and the mixture was stirred at 5° C. for 1 hour. To the reaction mixture was added an aqueous 10% hydrosulfite solution (30 g), and the mixture was stirred and separated to obtain an organic layer containing 2-amino-5-trifluoromethanesulfonylphenol. The yield was calculated by collecting a part of the organic layer and analyzing the organic layer by the internal standard method using high performance liquid chromatography. Yield 64%.

Example 3

A mixture, obtained by mixing 22.9 mmol (2.50 g) of 2-aminophenol, 25.2 mmol (3.90 g) of sodium trifluoromethanesulfinate, 25.2 mmol (4.09 g) of anhydrous iron (III) chloride and 25 g of acetic acid, was heated and stirred at 70° C. for 5 hours in the air. Apart of the reaction mixture was collected and analyzed using high performance liquid chromatography to confirm generation of 2-amino-5-trifluoromethanesulfonylphenol. Yield 50%.

Example 4-1

To a mixture, obtained by adding 2-aminophenol and 20.2 mmol (3.15 g) of sodium trifluoromethanesulfinate to 20 g of acetic acid, 20.2 mmol (1.94 g) of methanesulfonic acid was added dropwise and stirred at room temperature for 30 minutes. To the resulting mixture was added 40.4 mmol (9.21 g) of ammonium persulfate, and the mixture was heated and stirred at 50° C. for 10 hours. A part of the reaction mixture was collected and analyzed using high performance liquid chromatography to confirm generation of 2-amino-5-trifluoromethanesulfonylphenol.

Example 4-2

The same operation as described in Example 4-1 was carried out using copper(II) sulfate in place of ammonium persulfate to confirm generation of 2-amino-5-trifluoromethanesulfonylphenol.

Example 5-1

Under a nitrogen atmosphere, 2.75 mmol (450 mg) of anhydrous iron (III) chloride and 3 g of acetonitrile were mixed while cooling with an ice water bath, and 2.75 mmol (300 mg) of 2-aminophenol, 4.1 mmol (650 mg) of sodium trifluoromethanesulfinate and 5.5 mmol (530 mg) of methanesulfonic acid were added to the resulting mixture in this order, and then the mixture was stirred for 15 minutes. To this mixture was added 6.88 mmol (1.57 g) of ammonium persulfate, then the ice water bath was removed, and the mixture was stirred at 20° C. for 6 hours. To the reaction mixture was added 1.58 mmol (60 mg) of sodium borohydride, and the mixture was stirred for 30 minutes, then 3 g of water and 10 g of ethyl acetate were added thereto, and the mixture was stirred and separated to obtain an organic layer containing 2-amino-5-trifluoromethanesulfonylphenol. A part of this organic layer was collected and analyzed by the internal standard analysis method using high performance liquid chromatography to calculate the yield of 2-amino-5-trifluoromethanesulfonylphenol. Yield 300.

Example 5-2

The same operation as described in Example 5-1 was carried out using potassium persulfate in place of ammonium persulfate to confirm generation of 2-amino-5-trifluoromethanesulfonylphenol.

Example 6-1

A mixture, obtained by adding 0.5 mmol (0.078 g) of sodium trifluoromethanesulfinate, 0.25 mmol (0.027 g) of 2-aminophenol and 0.5 mmol (0.081 g) of anhydrous iron (III) chloride to 1 mL of acetic acid, was heated and stirred at 70° C. for 5 hours. Apart of the reaction mixture was collected and analyzed using high performance liquid chromatography to confirm generation of 2-amino-5-trifluoromethanesulfonylphenol.

Example 6-2

The same operation as described in Example 6-1 was carried out using the solvent, sulfinate and oxidizing agent described in Table 1 below. The results are shown below.

In Table 1, Table 2 and Table 3, $CF_3S(O)ONa$ represents sodium trifluoromethanesulfinate, $CF_3S(O)OK$ represents potassium trifluoromethanesulfinate, and $(CF_3S(O)O)_2Zn$ represents zinc bis(trifluoromethanesulfinate).

TABLE 1

| Solvent | Sulfinate | Oxidizing agent |
|---|---|---|
| Ethyl acetate | $CF_3S(O)ONa$ | Ammonium persulfate |
| 2-ethylhexanoic acid | $CF_3S(O)ONa$ | Potassium persulfate |

TABLE 1-continued

| Solvent | Sulfinate | Oxidizing agent |
| --- | --- | --- |
| 2-ethylhexanoic acid | $CF_3S(O)ONa$ | Anhydrous iron(III) chloride |
| Acetic acid | $CF_3S(O)OK$ | Iron(III) oxide |
| Acetic acid | $(CF_3S(O)O)_2Zn$ | 70% tert-butyl hydroperoxide |
| Acetic acid | $(CF_3S(O)O)_2Zn$ | Anhydrous iron(III) chloride |

Example 6-3

When the same operation as described in Example 6-1 was carried out using the combinations of solvent, sulfinate and oxidizing agent described in Table 2, 2-amino-5-trifluoromethanesulfonylphenol was obtained in any reaction.

TABLE 2

| Solvent | Sulfinate | Oxidizing agent |
| --- | --- | --- |
| Acetic acid | $CF_3S(O)Na$ | 30% hydrogen peroxide |
| 2-ethylhexanoic acid | $CF_3S(O)Na$ | 70% tert-butyl hydroperoxide |
| Acetic acid | $CF_3S(O)Na$ | 70% tert-butyl hydroperoxide |
| Acetic acid | $CF_3S(O)Na$ | Iron(III) chloride (hexahydrate) |
| Acetic acid | $CF_3S(O)Na$ | Iron(III) oxide |
| Acetic acid | $CF_3S(O)Na$ | Manganese dioxide |
| Acetic acid | $CF_3S(O)Na$ | Potassium hexacyanoferrate(III) |
| 10% aqueous sulfuric acid | $CF_3S(O)Na$ | Anhydrous iron(III) chloride |
| 3.5% aqueous hydrochloric acid | $CF_3S(O)Na$ | Anhydrous iron(III) chloride |
| DMF | $CF_3S(O)Na$ | Anhydrous iron(III) chloride |
| Acetonitrile | $CF_3S(O)Na$ | Anhydrous iron(III) chloride |
| Ethanol | $CF_3S(O)Na$ | Anhydrous iron(III) chloride |
| Acetic acid | $CF_3S(O)Na$ | Anhydrous iron(III) chloride |
| Ethyl acetate | $CF_3S(O)Na$ | Anhydrous iron(III) chloride |
| 10% aqueous sulfuric acid | $CF_3S(O)Na$ | Ammonium persulfate |
| 2-methyltetrahydrofuran | $CF_3S(O)Na$ | Ammonium persulfate |
| tert-butyl methyl ether | $CF_3S(O)Na$ | Ammonium persulfate |
| Acetonitrile | $CF_3S(O)Na$ | Ammonium persulfate |
| Ethanol | $CF_3S(O)Na$ | Ammonium persulfate |
| Cyclopentyl methyl ether | $CF_3S(O)Na$ | Ammonium persulfate |
| Methyl isobutyl ketone | $CF_3S(O)Na$ | Ammonium persulfate |
| Acetic acid | $CF_3S(O)Na$ | Ammonium persulfate |
| Acetic acid | $CF_3S(O)Na$ | 70%tBuOOH |
| 10% aqueous | $CF_3S(O)Na$ | Potassium persulfate |
| 2-methyltetrahydrofuran | $CF_3S(O)Na$ | Potassium persulfate |
| tert-butyl methyl ether | $CF_3S(O)Na$ | Potassium persulfate |
| Acetonitrile | $CF_3S(O)Na$ | Potassium persulfate |
| Xylene | $CF_3S(O)Na$ | Potassium persulfate |
| Cyclopentyl methyl ether | $CF_3S(O)Na$ | Potassium persulfate |
| Dimethylformamide | $CF_3S(O)Na$ | Potassium persulfate |
| Methyl isobutyl ketone | $CF_3S(O)Na$ | Potassium persulfate |
| Monochlorobenzene | $CF_3S(O)Na$ | Potassium persulfate |
| Acetic acid | $CF_3S(O)Na$ | Potassium persulfate |
| Ethyl acetate | $CF_3S(O)Na$ | Potassium persulfate |
| Acetic acid | $CF_3S(O)Na$ | Sodium hypochlorite |
| Acetic acid | $CF_3S(O)OK$ | 70% tert-butyl hydroperoxide |
| Acetic acid | $CF_3S(O)OK$ | Potassium persulfate |
| Acetic acid | $(CF_3S(O)O)_2Zn$ | Potassium persulfate |

Example 7-1

A mixture, obtained by adding 13.7 mmol (2.00 g) of 2-aminophenol hydrochloride, 15.1 mmol (2.36 g) of sodium trifluoromethanesulfinate and 30.2 mmol (6.90 g) of ammonium persulfate to 20 g of acetic acid, was heated and stirred at 70° C. for 10 hours under a nitrogen atmosphere. A part of the reaction mixture was collected and analyzed by high performance liquid chromatography to confirm generation of 2-amino-5-trifluoromethanesulfonylphenol.

Example 7-2

The same operation as described in Example 7-1 was carried out using potassium persulfate in place of ammonium persulfate to confirm generation of 2-amino-5-trifluoromethanesulfonylphenol.

Example 8-1

A mixture, obtained by adding 0.25 mmol (0.047 g) of 2-amino-3-methylphenol, 0.5 mmol (0.086 g) of sodium trifluoromethanesulfinate and 0.5 mmol (0.081 g) of anhydrous iron (III) chloride to 1 mL of acetic acid, was heated and stirred at 70° C. for 5 hours. Apart of the reaction mixture was collected and analyzed using high performance liquid chromatography to confirm generation of 2-amino-3-methyl-4-trifluoromethanesulfonylphenol.

Example 8-2

When the same operation as described in Example 8-1 was carried out using the sulfinate and oxidizing agent described in Table 3, generation of 2-amino-3-methyl-4-trifluoromethanesulfonylphenol was confirmed in any reaction.

TABLE 3

| Sulfinate | Oxidizing agent |
| --- | --- |
| $CF_3S(O)ONa$ | Potassium persulfate |
| $CF_3S(O)ONa$ | 70% tert-butyl hydroperoxide |

Reference Example 1

A mixture, obtained by adding 0.25 mmol (0.035 g) of 2-nitrophenol, 0.50 mmol (0.078 g) of sodium trifluoromethanesulfinate and 0.5 mmol (0.081 g) of anhydrous iron (III) chloride to 1 mL of acetic acid, was heated and stirred at 70° C. for 5 hours. When a part of the reaction mixture was collected and analyzed using high performance liquid chromatography, generation of 2-amino-3-methyl-4-trifluoromethanesulfonylphenol was not confirmed.

Reference Example 2

A mixture, obtained by adding 0.25 mmol (0.038 g) of 2-acetylaminophenol, 0.078 g (0.50 mmol) of sodium trifluoromethanesulfinate and 0.5 mmol (0.081 g) of anhydrous iron (III) chloride to 1 mL of acetic acid, was heated and stirred at 70° C. for 5 hours. When a part of the reaction mixture was collected and analyzed using high performance liquid chromatography, generation of 2-amino-3-methyl-4-trifluoromethanesulfonylphenol was not confirmed.

INDUSTRIAL APPLICABILITY

A perfluoroalkanesulfonylphenol compound useful as a production intermediate of pharmaceuticals and agrochemicals can be manufactured by the present invention.

The invention claimed is:
1. A method for producing a compound represented by formula (3):

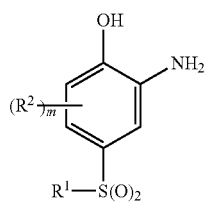
(3)

wherein $R^1$ represents a C1-C6 perfluoroalkyl group, $R^2$ represents a C1-C6 alkyl group, and m represents an integer of 0 to 3, or a salt thereof, comprising reacting an alkali metal salt or zinc salt of a C1-C6 perfluoroalkanesulfinic acid with 2-aminophenol optionally substituted by 1 to 3 C1-C6 alkyl groups or a salt thereof in the presence of an oxidizing agent.

2. The method according to claim 1, wherein the oxidizing agent is one or more oxidizing agents selected from the group consisting of persulfates, peroxides, trivalent iron compounds, divalent copper compounds and manganese compounds.

3. The method according to claim 1, wherein the oxidizing agent is one or more oxidizing agents selected from the group consisting of potassium persulfate, ammonium persulfate, tert-butyl hydroperoxide, iron(III) chloride, iron(III) oxide, manganese dioxide and copper(II) sulfate.

4. The method according to claim 1, wherein $R^1$ is a C1-C3 perfluoroalkyl group.

5. The method according to claim 1, wherein $R^1$ is a trifluoromethyl group.

6. The method according to claim 1, comprising reacting a sodium salt or potassium salt of a C1-C6 perfluoroalkanesulfinic acid.

7. The method according to claim 5, comprising reacting a sodium salt or potassium salt of trifluoromethanesulfinic acid.

8. The method according to claim 1, comprising reacting an alkali metal salt or zinc salt of a C1-C6 perfluoroalkanesulfinic acid with 2-aminophenol optionally substituted by 1 to 3 C1-C6 alkyl groups or a salt thereof in the presence of an oxidizing agent, by adding sulfuric acid, methanesulfonic acid or hydrochloric acid.

* * * * *